United States Patent [19]

Stolar

[11] 4,062,940
[45] Dec. 13, 1977

[54] WATER-SOLUBLE COMPOSITION COMPRISING SULFADIMIDINE AND PYRIMETHAMINE

[75] Inventor: Morris E. Stolar, Tel Aviv, Israel

[73] Assignee: Abic Ltd., Israel

[21] Appl. No.: 786,043

[22] Filed: Apr. 8, 1977

[30] Foreign Application Priority Data

Apr. 14, 1976 Israel ........................................ 49412

[51] Int. Cl.$^2$ .................... A61K 31/79; A61K 31/635
[52] U.S. Cl. ........................................ 424/80; 424/229
[58] Field of Search ................................. 424/80, 229

[56] References Cited

U.S. PATENT DOCUMENTS

| 3,728,452 | 4/1973 | Haber et al. | 424/229 |
| 3,985,876 | 10/1976 | Hazlett et al. | 424/229 |

Primary Examiner—Sam Rosen
Attorney, Agent, or Firm—Steinberg & Blake

[57] ABSTRACT

There are disclosed water-soluble compositions comprising sulfadimidine sulfate, polyviylpyrrolidine (PVP) and a physiologically acceptable water-soluble salt of pyrimethamine. Said compositions may comprise also a filler substance. There are also disclosed aqueous suspensions comprising the above composition and a method for the treatment of animals suffering from bacterial infections.

11 Claims, No Drawings

WATER-SOLUBLE COMPOSITION COMPRISING SULFADIMIDINE AND PYRIMETHAMINE

The present invention relates to a water-soluble powderous composition of N-(4,6-dimethyl-2-pyrimidinyl)-sulfanilamide (hereinafter called "sulfadimidine") and 2,4-diamino-5-(p-chlorophenyl-6-ethyl-pyrimidine (hereinafter called "pyrimethamine").

It is known that both sulfadimidine and pyrimethamine are utilised in the treatment of diseased animals, in particular poultry, suffering from bacterial infections, such as those caused by Salmonella, Pasteurella, *Haemophylus gallinarum*, Coli, etc. as well as in the treatment of animals infected by the protozoal disease coccidiosis.

Moreover, it is known that pyrimethamine and sulfadimidine have a synergistic effect on each other (see for example Kendall and Joyner, J. Comp. Path. 1956, Vol. 66, pages 145–150) when being utilised in treating animals infected by diseases as indicated above.

Sulfadimidine and pyrimethamine are both practically water insoluble and have if used as such to be administered as part of the feed to the animals. However, when animals are ill, i.e., when the administration of said compounds is required, they usually do not accept the usual amounts of food. On the other hand they generally continue to drink water in this state of health.

The sodium salt of sulfadimidine is water-soluble and may be administered to the animals as part of the drinking water. However, said sodium salt has a bitter taste and chicks are reluctant to drink water containing effective quantities of the sodium salt of sulfadimidine as said quantities are quite high.

Pyrimethamine can be converted into certain acid addition salts, e.g., hydrochloride, tartate, etc., which are also water soluble.

Thus, both sulfadimidine and pyrimethamine can be converted into water soluble salts. However, it is readily understood that mixing aqueous solutions of the sodium salt of sulfadimidine and of an acid addition salt of pyrimethamine will cause interactions of the two salts resulting in the precipitation of both sulfadimidine and pyrimethamine and leaving sodium chloride in solution.

From British Patent Specification No. 1,176,395 there is known an injectable composition which comprises an aqueous solution of a water-soluble salt of a sulphonamide with a solution of a basically-reacting organic compound which acts as a sulphonamide-patentiator, e.g. a pyrimidine derivative in a medicinally acceptable water miscible organic solvent. However, said composition utilises a salt of the sulphonamide, which in the case of sulfadimidine is very undesirable as set out before.

Moreover, from Israel Patent Specification No. 33774 there is known a water-soluble composition comprising sulfadimidine, pyrimethamine and a solvent selected among the group consisting of propylene, glycol, tetraglycol, polyethylene glycol, Carbowax and glycerol formal.

The above composition can be administered as part of the drinking water but has certain other disadvantages, namely:
1. The composition is a liquid which is usually not desirable as it requires excessive storage area and excessive transport costs;
2. The composition requires certain organic solvents which are relatively expensive.

It has therefore been desirable to find a composition which would be a powder the solubility of which would be high enough to ascertain its use in any desired concentration and in particular its use with a proportional pump.

From South African Patent Secification No. 68.03272 it is known that certain salts of some sulphonamides, inter alia, sulfadimidine, are slightly soluble in water and their solubility is increased by the addition of tetracycline.

It has been found that the solubility of sulfadimidine sulphate in water is about 1.23% whereas the solubility of the other salts of sulfadimidine e.g., the hydrochloride and the nitrate, is slightly lower.

It is known that the addition of polyvinylpyrrolidine (hereinafter called "PVP") increases the solubility of some chemical substances to a certain extent. However, the increase is usually only of about a few percentages. It has now been found that the solubility of sulfadimidine sulphate in water is increased to about 10 −30% when PVP is added. (The increase depends on the amount of PVP added). This was rather an unexpected result as the same effect could not be observed for the hydrochloride or any other salt of sulfadimidine or for any salt or other sulphonamides, e.g. sulfanylamide.

As indicated above the solubility of certain salts of pyrimethamine is known.

The present invention thus consists in a water-soluble powderous composition comprising sufadimidine sulfate, PVP and a physiologically acceptable water-soluble salt of pyrimethamine.

Although the composition according to the present invention may comprise only the above compounds it is sometimes desirable to add certain other compounds, e.g. fillers, etc. As suitable fillers there may be mentioned, inter alia, sugar, sodium chloride, etc.

The compound according to the present invention comprises suitably 7–80% of sulfadimidine sulfate, 0.7–25% PVP and 0.7–10% of the pyrimethamine salt, if desired, the residue being a filler substance.

In a preferred embodiment of the invention the composition comprises 65–75% of sulfadimidine sulfate; 7–9% PVP and 7–10% of the pyrimethamine salt, and if desired, the residue being a filler substance.

The composition according to the present invention is prepared by mixing the various ingredients together by methods known per se. In order to obtain a better mixing said ingredients are screened before mixing through a 20 mm mesh screen. It has been found that when the composition is dissolved in a suitable amount of water, a solution is obtained which is stable for at least 24 hours.

The present invention will now be described with reference to the following examples without being restricted by them.

EXAMPLE 1

100 g of concentrated sulfuric acid were added gradually with great caution to 220 ml of water. The solution was stirred and 222 g of sulfadimidine were added gradually with stirring and the reaction mixture was heated to 60°–70° C. Stirring was continued until all the sulfadimidine had dissolved. The mixture was then cooled to 40° C and poured with stirring into 400 ml of isoproponol. Stirring was continued until precipitation started. The precipitated sulfadimidine sulfate was filtered off, washed with isoproponol and dried. Yield 91–95% of the theory.

EXAMPLE 2

60 g of tartaric acid were dissolved in 600 ml of ethanol. 100 g of pyrimethamine were added with stirring. The mixture was cooled to 35°-40° C and then acetone was added. Stirring was continued until precipitation started. The precipitated pyrimethamine tartrate was filtered off, washed with acetone and dried. Yield 95.9% of the theory.

In a similar manner other suitable pyrimethamine salts, e.g. pyrimethamine hydrochloride, were prepared.

EXAMPLE 3

The following composition was prepared by a simple mixing procedure after each ingredient had been sieved through a 20 mm mesh screen.
Sulfadimidine sulfate: 71 g
Pyrimethamine tartrate: 8 g
PVP: 8 g
NaCl: 13 g 2 g of the above composition were dissolved in 1 L of water. The solution was stable for some days.

EXAMPLE 4

The following composition was prepared:
Sulfadimidine sulfate: 71.0 g
Pyrimethamine HCl: 5.71 g
PVP: 8.5 g
Sugar: 14.79 g Similar amounts as indicated in Example 3 were used and a satisfactory effect was observed.

EXAMPLE 5

The following composition was prepared:
Sulfadimidine sulfate: 35.5 g
Pyrimethamine HCl: 2.85 g
PVP: 2.0 g
Sugar: 59.65 g 4 g of the above composition were dissolved in 1 L of water. The solution was stable for some days.

EXAMPLE 6

The following composition was prepared:
Sulfadimidine sulfate: 7.0 g
Pyrimethamine Tartate: 0.8 g
PVP: 0.1 g
Sugar: 92.1 g 20 g of the above composition were dissolved in 1 L of water. The solution was stable for some days.

EXAMPLE 7

The following composition was prepared:
Sulfadimidine sulfate: 75 g
Pyrimethamine HCl: 10 g
PVP: 15 g Similar amounts as indicated in Example 3 were used and a satisfactory effect was observed.

I claim:
1. A water-soluble powderous composition comprising sulfadimidine sulfate, PVP and a physiologically acceptable water soluble salt of pyrimethamine.
2. A composition according to claim 1, comprising a filler substance.
3. A composition according to claim 2, wherein the filler substance is sugar.
4. A composition according to claim 2, wherein the filler substance is sodium chloride.
5. A composition according to claim 1 wherein the pyrimethamine salt is the tartrate.
6. A composition according to claim 1 wherein the pyrimethamine salt is the hydrochloride.
7. A composition according to claim 1 comprising 7-80% of sulfadimidine sulfate, 0.7-25% PVP and 0.7-10% of the pyrimethamine salt and, if desired, the residue being a filler substance.
8. A composition according to claim 7 comprising 65-75% of sulfadimidine sulfate, 7-9; PVP and 7-10% of the pyrimethamine salt and, if desired, the residue being a filler substance.
9. An aqueous solution comprising a composition according to claim 1 dissolved in water.
10. An aqueous solution according to claim 9 wherein each liter of water comprises 0.1-40 g of said composition.
11. A method for the treatment of animals suffering from bacterial infections in which a composition according to claim 1 is administered as part of the drinking water.

* * * * *